United States Patent
Izatt et al.

(10) Patent No.: US 7,719,692 B2
(45) Date of Patent: May 18, 2010

(54) METHODS, SYSTEMS AND COMPUTER PROGRAM PRODUCTS FOR OPTICAL COHERENCE TOMOGRAPHY (OCT) USING AUTOMATIC DISPERSION COMPENSATION

(75) Inventors: Joseph A. Izatt, Raleigh, NC (US); Eric L. Buckland, Hickory, NC (US); William J. Brown, Durham, NC (US)

(73) Assignee: Bioptigen, Inc., Durham, NC (US)

( * ) Notice: Subject to any disclaimer, the term of this patent is extended or adjusted under 35 U.S.C. 154(b) by 348 days.

(21) Appl. No.: 11/796,399

(22) Filed: Apr. 27, 2007

(65) Prior Publication Data

US 2007/0258094 A1 Nov. 8, 2007

Related U.S. Application Data

(60) Provisional application No. 60/795,790, filed on Apr. 28, 2006.

(51) Int. Cl.
*G01B 11/02* (2006.01)
(52) U.S. Cl. .................................... 356/497
(58) Field of Classification Search .......... 356/479, 356/497
See application file for complete search history.

(56) References Cited

U.S. PATENT DOCUMENTS

| | | |
|---|---|---|
| 7,113,288 B2 | 9/2006 | Fercher |
| 7,301,644 B2 | 11/2007 | Knighton et al. |
| 2005/0018201 A1 | 1/2005 | de Boer et al. |
| 2005/0280828 A1 | 12/2005 | Fitzgerald de Boer |
| 2007/0002327 A1 | 1/2007 | Zhou et al. |
| 2007/0291277 A1 | 12/2007 | Everett et al. |

FOREIGN PATENT DOCUMENTS

| | | |
|---|---|---|
| WO | WO 2005/117534 A2 | 12/2005 |
| WO | WO2005/117534 A2 | 12/2005 |

OTHER PUBLICATIONS

Cense et al. "Ultrahigh-resolution high-speed retinal imaging using spectral-domain optical coherence tomography" *Optics Express* 12(11):2435-2447 (2004).
International Search Report and Written Opinion for PCT/US2007/010286; Nov. 21, 2007.
Wojtkowski et al. "Ultrahigh-resolution, high-speed, Fourier domain optical coherence tomography and methods for dispersion compensation" *Optics Express* 12(11):2404-2422 (2004).

(Continued)

*Primary Examiner*—Tarifur Chowdhury
*Assistant Examiner*—Jonathon D Cook
(74) *Attorney, Agent, or Firm*—Myers Bigel Sibley & Sajovec (57) ABSTRACT

Methods, systems and computer program products for generating parameters for software dispersion compensation in optical coherence tomography (OCT) systems are provided. Raw spectral interferogram data is acquired for a given lateral position on a sample and a given reference reflection. A trial spectral phase corresponding to each wavenumber sample of the acquired spectral interferogram data is postulated. The acquired raw spectral data and the postulated trial spectral phase data are assembled into trial complex spectrum data. Trial A-scan data is computed by performing an inverse Fourier transform on the trial complex spectrum data and determining the magnitude of a result.

18 Claims, 7 Drawing Sheets

OTHER PUBLICATIONS

Cense et al., "Ultrahigh-resolution high-speed retinal imaging using spectral-domain optical coherence tomography," Optics Express, vol. 12, No. 11, May 31, 2004, pp. 2435-2447.

Wojtkowski et al., "Ultrahigh-resolution, high-speed, Fourier domain optical coherence tomography and methods for dispersion compensation," Optics Express, vol. 12, No. 11, ay 31, 2004, pp. 2404-2422.

Figure 6

METHODS, SYSTEMS AND COMPUTER PROGRAM PRODUCTS FOR OPTICAL COHERENCE TOMOGRAPHY (OCT) USING AUTOMATIC DISPERSION COMPENSATION

CROSS-REFERENCE TO RELATED APPLICATION

The present application claims priority from U.S. Provisional Application No. 60/795,790, filed Apr. 28, 2006, the disclosure of which is hereby incorporated herein by reference as if set forth in its entirety.

STATEMENT OF GOVERNMENT SUPPORT

This invention was made with government support under grant number 2R44EY015585 awarded by National Institutes of Health, National Eye Institute. The United States Government has certain rights in this invention.

FIELD OF THE INVENTION

The present invention relates to imaging and, more particularly, to optical coherence tomography (OCT) and related methods, systems and computer program products.

BACKGROUND OF THE INVENTION

Optical Coherence Tomography (OCT) is technique for imaging into samples, such as tissue, glass and the like. Recent advances in OCT include Fourier Domain (FD)-OCT, in which either a broadband source with a spectrometer (SD-OCT) or a swept laser source with a single photodiode (SS-OCT) is used to generate OCT images. These OCT architectures may be dependent on the dispersion properties of a reference arm and a sample arm, particularly the relative variation in dispersion between the two arms. This variation in dispersion can be compensated either by changing the optical properties of the sample or reference arm or by using numerical compensation techniques in the OCT processing and imaging software. This numerical compensation may require one or more parameters for the dispersion management.

Figure 1:
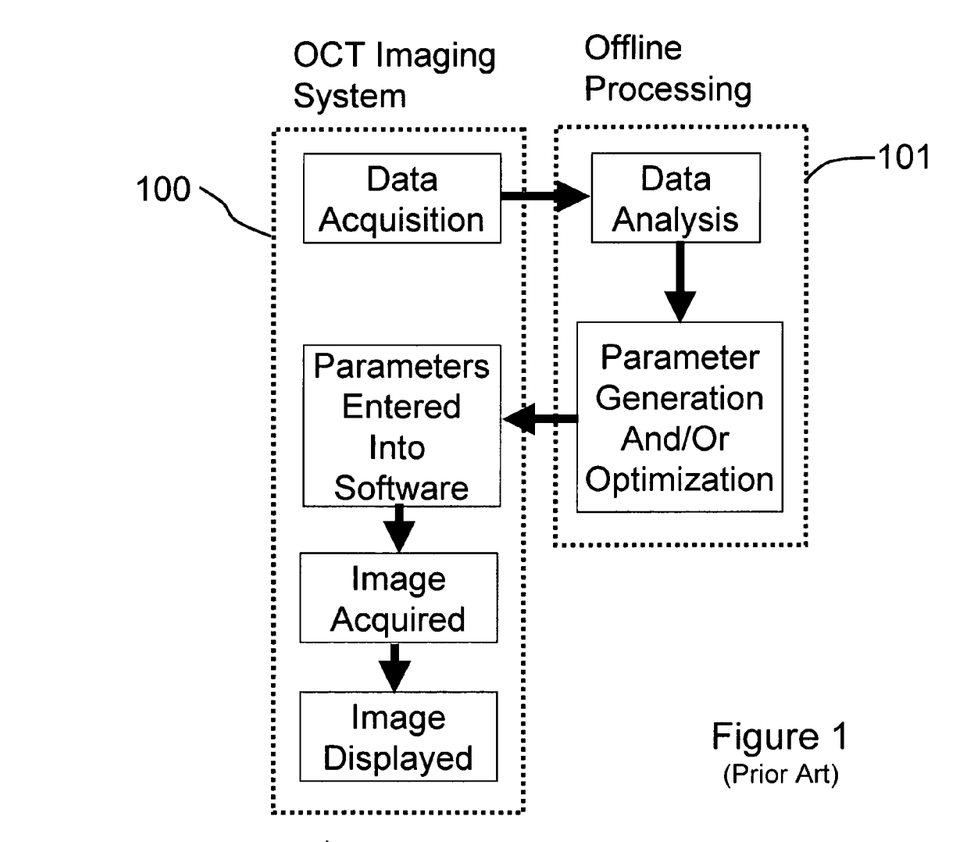
FIG. 1 is a schematic block diagram illustrating a conventional technique for dispersion parameter optimization.

Referring now to FIG. 1, a schematic block diagram illustrating a conventional technique for dispersion parameter optimization will be discussed. As illustrated in FIG. 1, the system includes and OCT imaging system 100 and Offline processing 101. As further illustrated in FIG. 1, the OCT imaging system 100 may be used for data acquisition, entering the parameters into the software, acquiring the image and displaying the image. The Offline Processor 101 may be used to analyze the data acquired by the OCT system 100 and generate/optimize the parameters entered into the OCT imaging system 100. Using conventional methods, the one or more parameters typically may be determined either by trial and error, for example, the system user may try various values until an optimal parameter value is determined. Alternatively, offline or post processing 101 associated with the OCT imaging system 100 may be used to search for the optimal parameter values. Conventional processes are discussed in, for example, ULTRAHIGH-RESOLUTION HIGH SPEED RETINAL IMAGING USING SPECTRAL-DOMAIN OPTICAL COHERENCE TOMOGRAPHY by Teresa C. Chen (Optics Express, Volume 12, No. 11, May 31, 2004) and Ultrahigh-resolution, high-speed, FOURIER DOMAIN OPTICAL COHERENCE TOMOGRAPHY AND METHODS FOR DISPERSION COMPENSATION by Wojtkowski et al. (Optics Express, Volume 12, No. 11, May 31, 2004), the disclosures of which are incorporated herein by reference as if set forth in their entirety.

Two separate dispersion compensation algorithms are discussed in Wojtkowski. The first involves re-scaling of raw spectrum data during interpolation of SDOCT data from wavelength space to wavenumber space. This algorithm may provide fast results, since it does not involve complex computation, but the results may not be accurate, since it only corrects dispersion at a single depth in the sample.

According to the second algorithm discussed in Wojtkowski, the corrected spectrum data is obtained from a Hilbert transform of the raw spectrum modified by optimized phase correction parameters. This algorithm may provide accurate results, since it corrects dispersion for all depths in the sample simultaneously, but the results are not provided fast, since the Hilbert transform process as proposed is a computationally complex operation involving multiple forward and inverse Fourier transformations.

Thus, the processes discussed with respect to FIG. 1 and in the Chen and Wojtkowski references may be inaccurate (providing sub-optimal images), excessively time consuming (thus possibly preventing real time system operation), or may require detailed information regarding the specific dispersion properties of the system optics and/or each sample to be imaged. Accordingly, improved methods of numerical dispersion compensation may be desired.

SUMMARY OF THE INVENTION

Some embodiments of the present invention provide methods, systems and computer program products for generating parameters for software dispersion compensation in optical coherence tomography (OCT) systems. Raw spectral interferogram data is acquired for a given lateral position on a sample and a given reference reflection. A trial spectral phase corresponding to each wavenumber sample of the acquired spectral interferogram data is postulated. The acquired raw spectral data and the postulated trial spectral phase data are assembled into trial complex spectrum data. Trial A-scan data is computed by performing an inverse Fourier transform on the trial complex spectrum data and taking the magnitude of a result.

In further embodiments of the present invention, the raw spectral interferogram data may be denoted M(k). Postulating a trial phase corresponding to each wavenumber sample of M(k) may be done according to the following equation:

$$\phi(k) = a(k-k_0) + b(k-k_0)^2 + c(k-k_0)^3 + d(k-k_0)^4,$$

wherein $k_0$ is the central wavenumber of a light source of the OCT system, and wherein a, b, c and d are parameters to be optimized and represent respective first, second, third, and fourth-order corrections to be made to a phase of the acquired raw spectral interferogram data.

In still further embodiments of the present invention, assembling may include assembling the acquired raw spectral interferogram data and the trial spectral phase data into the trial complex spectrum data according to the following equation:

$$S(k) = M(k)e^{i\phi(k)},$$

wherein e is the base of natural logarithms and i is the square root of −1.

In some embodiments of the present invention, computing may include computing trial A-scan data by performing an inverse Fourier transform on the trial complex spectrum data and taking the magnitude of the result according to the following equation:

$$|s(z)|=|I.F.T.\{S(k)\}|,$$

wherein the result |s(z)| is the real-valued trial A-scan representing the depth-resolved reflectivity of the sample at a given lateral location, blurred by dispersion mismatch between interferometer arms but corrected by the postulated trial spectral phase.

In further embodiments of the present invention, the postulating, assembling and computing steps may be repeated to optimize the values of a, b, c and d based on optimization of an image quality metric applied to the trial A-scan data |s(z)|. In certain embodiments of the present invention, the result may be depth independent.

Still further embodiments of the present invention provide methods, systems and computer program products for generating parameters for software dispersion compensation in optical coherence tomography (OCT) systems. Optimization of parameters for software dispersion compensation is initiated. The parameters are optimized in less than about 15 seconds. An image is processed using the optimized parameters without increasing processing time relative to the processing of an image without implementing dispersion optimization parameters.

In some embodiments of the present invention, the parameters may be optimized in from about 3.0 to about 5.0 seconds. In certain embodiments of the present invention, an entire depth of the sample may be optimized.

DETAILED DESCRIPTION OF EMBODIMENTS OF THE INVENTION

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and should not be interpreted in an idealized or overly formal sense unless expressly so defined herein.

As will be appreciated by one of skill in the art, the invention may be embodied as a method, data processing system, or computer program product. Accordingly, the present invention may take the form of an entirely hardware embodiment, an entirely software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language or in a visually oriented programming environment, such as VisualBasic.

The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The invention is described in part below with reference to a flowchart illustration and/or block diagrams of methods, systems and computer program products according to embodiments of the invention. It will be understood that each block of the illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Some embodiments of the present invention will now be discussed with respect to FIGS. 1 through 6. As discussed with respect thereto, some embodiments of the present invention may provide an automatic dispersion compensation optimization where the OCT imaging software searches for the optimal value(s) relatively quickly when triggered by the user and/or by a condition in the software. Many optimization metrics can be used, for example, maximizing the brightest spot or line in the image or by maximizing the number of lines or spots in the image with intensity that may exceed some specified threshold. It will be understood that various computational architectures can be used to implement embodiments of the present invention and, therefore, embodiments of the present invention should not be limited to the computational architectures described herein.

As discussed herein, some embodiments of the present invention provide hardware and/or software systems, methods and computer program products that use search or optimization routines to find parameters for software dispersion compensation in OCT systems in real time. Various embodiments of the present invention are described below including multiple hardware and/or software configurations for finding and using these optimized dispersion parameters. It will be understood that the configurations discussed herein are provided for exemplary purposes only and, therefore, embodiments of the present invention should not be limited thereby.

OCT imaging systems may typically be categorized in two general categories, time domain (TD)-OCT, where a moving mirror or prism in the reference arm determines the current imaging depth location in the sample, and Fourier domain (FD)-OCT, where the reference arm is fixed in length and data is acquired over a spectrum of wavelengths to change imaging depth location in the sample. FD-OCT is typically further categorized into two categories, swept source (SS)-OCT (SS-OCT) and spectral domain (SD)-OCT. For SS-OCT, a narrow-line width laser is typically swept in wavelength over time to interrogate the sample at different wavelengths. For SD-OCT, a broad band (low coherence) source, such as a superluminescent diode (SLD), is typically used in conjunction with a spectrometer. Various embodiments of the present invention may be used with any of these hardware implementations without departing from the scope of the present invention.

OCT systems typically operate by acquiring depth data at a particular point on the sample, which may be called an A-scan. The OCT beam is moved relative to the sample using, for example, any of the various depth adjustment approaches described above, and another set of depth data may be acquired. These series of depth images are put together to form a 2-D image, which may be called a B-scan. Any scan pattern can generally be used, where commonly used scan patterns include, for example, linear and circular. By scanning in two directions instead of just one, a 3-D volume of data can be acquired. Again any scan pattern can generally be used, where commonly used 3-D scan patterns include, for example, rectangular, sets of radial lines, and sets of concentric circles.

OCT data is a measurement of the reflectivity at each depth in the sample at a given point. In other words, the contrast in the image is generally due to variations in the reflectivity in the sample. Other contrast mechanisms may be used without departing from the scope of the present invention. For example, polarization contrast and spectral contrast may be used.

A property of most OCT systems is that the image quality may be affected by the relative dispersion of the sample and reference paths. Uncompensated dispersion typically shows up as blurring in the OCT image. There are multiple methods that can be used to compensate for dispersion. For example, the physical properties of the sample or reference path may be changed to make the dispersion in the two arms identical or nearly so. This technique has some drawbacks. For example, in retinal imaging the sample path includes approximately one inch of water in the aqueous and vitreous humor in the eye so the reference path also needs one inch of compensating water. Building a robust water cell may add significant complexity and cost of the OCT system. Furthermore, when the sample path is partially in the sample, as is the case in the retina, changing from one subject to another may change the dispersion properties of the overall system and may require different compensation.

Another technique for dispersion compensation is to numerically compensate for the dispersion as the OCT image processing is done. Typically, in SD-OCT systems, the data from the spectrometer is re-sampled so that it is evenly spaced in wavenumber instead of being evenly space in wavelength. When this calculation is done, the dispersion compensation may show up as higher order terms in the resampling equation. For SS-OCT systems, a resampling may or may not be required depending on the system design, but regardless, the dispersion compensation can typically be performed. This numerical dispersion compensation is dependent on the accuracy of the parameters used in the numerical compensation; inaccurate values may still result in blurred images.

These dispersion compensation parameter(s) can be determined by a variety of techniques. For example, the user may enter a set of parameters, look at the resulting image and change the parameters. In other words, the user may try to get the best image by looking at the image for various values of the dispersion parameter(s). This technique is typically slow, unreliable and hard to repeat. A more accurate technique is a take a line or frame of OCT data and run it through another program, which searches for the best dispersion parameters. This program is typically, but need not be, separate from the program that acquired the raw data and transforms it into OCT images. The search program can be built in a variety of ways particularly in the search and in the optimization metric. For this type of search, a metric is typically defined and the search tries to optimize the value of the metric. Any of a number of metrics can be used. In addition, the method used to search the parameter space can be accomplished by a variety of techniques or schemes. For example, the search may be conducted on a separate machine from where the imaging is occurring and may take several minutes to transfer the raw OCT data, run the optimization software, and transfer the dispersion compensation parameters back to the OCT imaging program. The delay induced by this process may be undesirable.

Figure 2A:
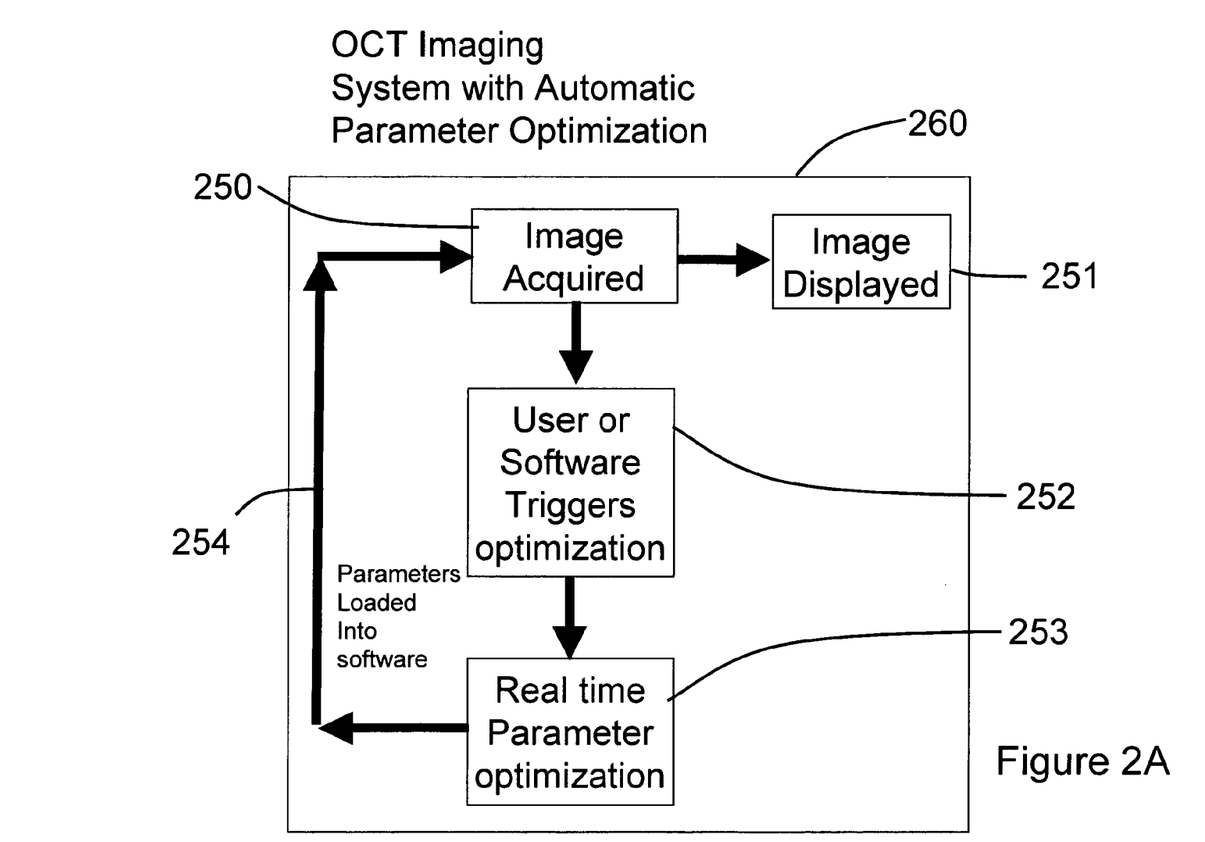
FIG. 2A is a conceptual block diagram illustrating OCT imaging software according to some embodiments of the present invention.

Referring now to FIG. 2A, a conceptual block diagram illustrating OCT imaging methods, systems and computer program products according to some embodiments of the present invention will be discussed. As illustrated in FIG. 2A, the dispersion algorithm according to some embodiments of the present invention is integrated with the OCT imaging program, thereby potentially reducing the likelihood that an off-line determination of dispersion parameters will be needed. In particular, the OCT imaging software module 260 according to some embodiments of the present invention includes a software module that triggers optimization of the parameters 252, a software module that actually optimizes the parameters 253, a software module that acquires an image 250 after the parameters are loaded 254 and a software module that processes and displays the images 251. Many of these steps may be performed using an algorithm. Exemplary algorithms according to some embodiments of the present invention will be discussed below with respect to the flowchart of FIG. 6.

Figure 2B:
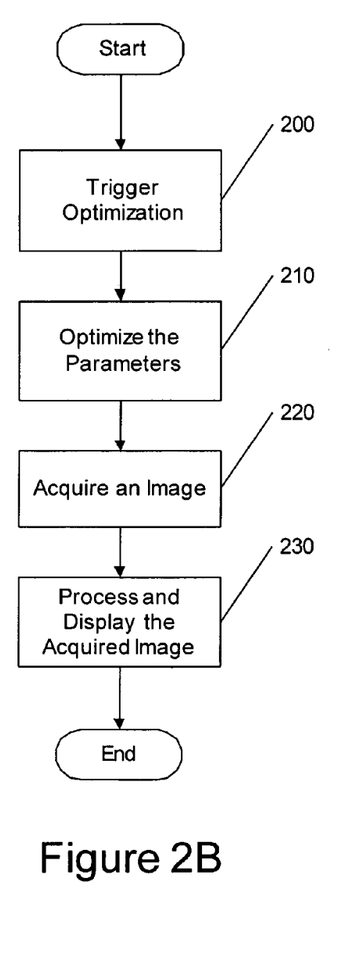
FIG. 2B is a flowchart illustrating operations of OCT imaging methods, systems and computer program products using automatic dispersion parameter optimization according to some embodiments of the present invention.

Operations of OCT imaging systems according to some embodiments of the present invention will now be discussed with respect to the flowchart of FIG. 2B. As discussed above, OCT imaging software is configured to provide dispersion parameter optimization. In particular, operations of the OCT imaging software according to some embodiments of the present invention begin at block 200 by triggering optimization. The optimization may be triggered by, for example, the user, by some condition in the software, such as for each acquisition line, each frame, each volume, once a day, once an hour, once an image set and the like and/or a combination of thereof. Once the optimization is triggered, the software switches from image acquisition and display and the parameters may be optimized (block 210). It typically takes from about a few seconds to about a few tens of seconds to find the optimal dispersion compensation parameters with typical commercial central processing units (CPUs), though this speed may be, in principle, reduced to beneath a single line acquisition time frame. Once the parameters are optimized, the parameters may be transferred to the imaging portion of the system, where the image may be acquired (block 220) and displayed (block 230).

When the optimization is triggered, the software takes some of the recently acquired data and uses it to optimize the dispersion parameters. This may be accomplished by starting with a set of parameters, calculating an image, measuring some metric regarding at least some portion of the image, adjusting the set of parameters, and repeating. The goal is to maximize (or minimize) the metric while searching through the parameter space. As used herein, "maximize" and "minimize" refer to getting close to the maximum and/or minimum, but not necessarily achieving an absolute maximum and/or minimum. One metric that can be used includes finding the brightest spot or line in the image and making it as bright as possible. Another metric that may be used is to maximize the number of lines or spots that are above some fixed or variable threshold level. Still another metric that may be used is to maximize another aspect of the intensity distribution function.

The remaining portion of the software routine is how the parameter space is searched to optimize the given metric. Any number of search algorithms may work and, therefore, embodiments of the present invention are not limited to the algorithms described herein. For example, a set step search may be conducted one parameter at a time. The most significant parameter may be searched first. The search starts at a specified number and takes steps of a set size until the metric passes through a maximum (or minimum). Then the search switches to a binary search where the two points around the maximum are used as the starting point and then a point half way in between is checked. The midpoint and the highest end point become the starting values for the next iteration. Once the most significant parameter is optimized, the next parameter is optimized using the same technique. This may work for any number of parameters.

According to further embodiments of the present invention, a strict binary search may be used for all parameters by setting an initial upper and lower limit on the parameter value and searching within that space for the optimal value. According to still further embodiments of the present invention, parameters may be iteratively reoptimized as each parameter is adjusted. For example if there are two parameters, A and B; A would be optimized, B would be optimized, then A would be reoptimized based on the new value of B and B would be reoptimized based on the new value of A. This can be done for a set number of iterations or until some metric is satisfied, such as the change in A and B after a reoptimization is less than a given level.

In general, dispersion parameters consist of an ordered set of sequentially higher order terms. The lowest order term is substantially equivalent to the refractive index of the material, and impacts the length scaling of the image. The next three higher order terms are the first, second, and third derivatives of the refractive index with respect to frequency (or wavelength). Implementations of the dispersion optimization algorithm may include optimizing one, two, or three of these terms. Further, the optimization may include sequentially optimizing each ordered term independently, searching for the next higher order term only after the preceding term has been optimized. Alternatively, a multi-dimensional global optimization routine may be deployed, although this may be computationally costly and may be without added benefit. Generally, use of a fourth order or higher term is not required, but can be performed without departing from the scope of the present invention.

Figure 3:
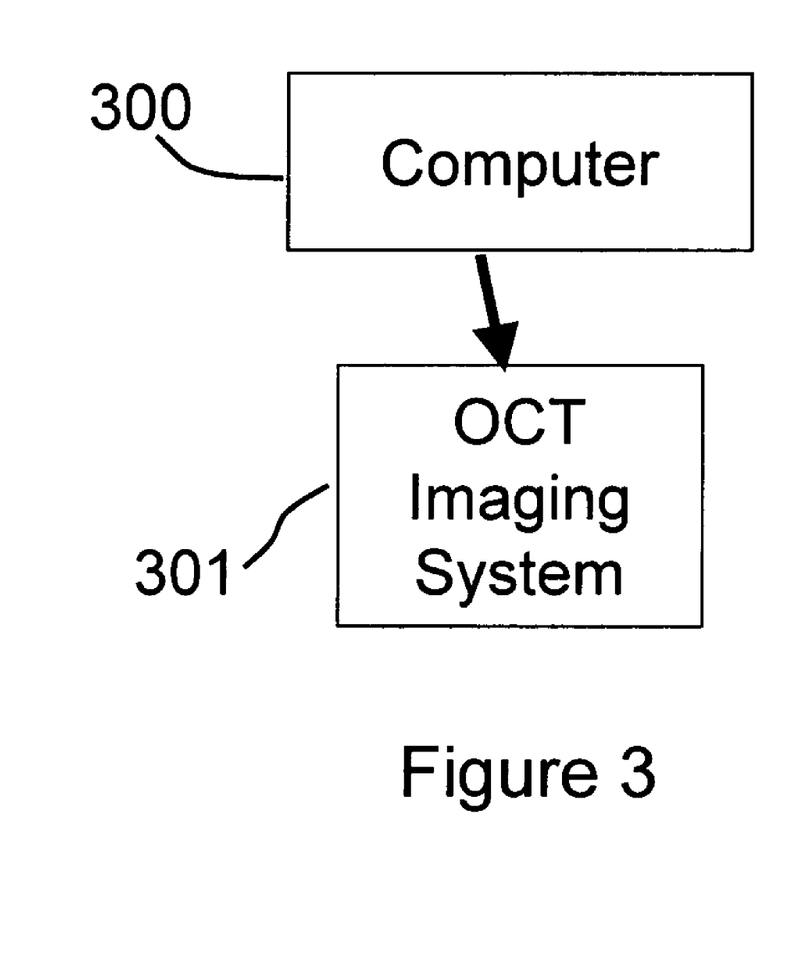
FIG. 3 is a schematic diagram illustrating systems according to some embodiments of the present invention.

Some embodiments of the present invention will now be discussed with reference to the schematic block diagram of FIG. 3. As illustrated in FIG. 3, a computer 300 running software is connected to an OCT imaging system 301. The computer executes software that may be resident in memory. Various software modules in the memory may, among other things, process raw data to create OCT image datasets, for example, A-scans, B-scans and/or volume images, display data to a user monitor (or the like), store data, and optimize various parameters for dispersion compensation or other affects.

Figure 4:
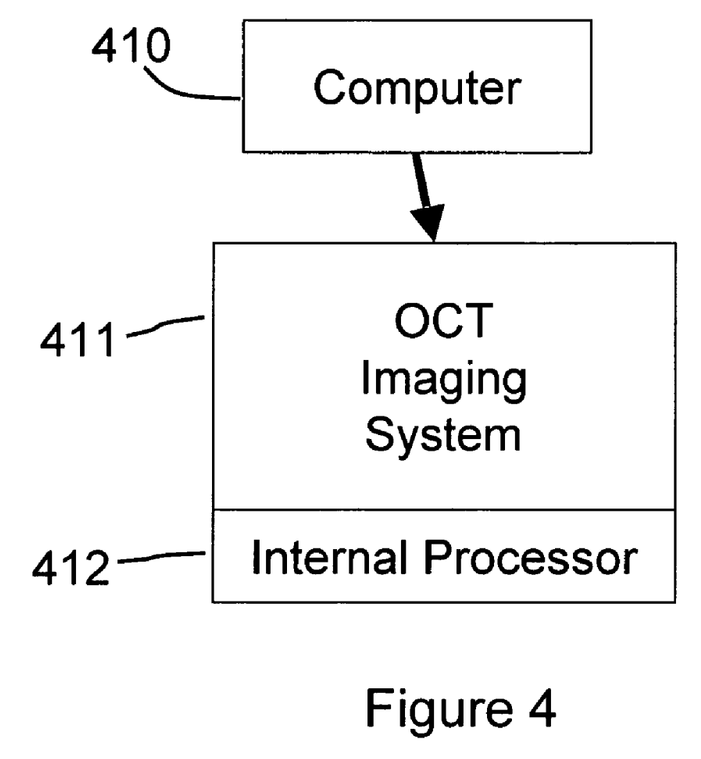
FIG. 4 is a schematic diagram illustrating systems according to further embodiments of the present invention.

Further embodiments of the present invention will now be discussed with respect to FIG. 4. As illustrated in FIG. 4, the computer 410 running software interfaces with an OCT imaging system 411 that includes internal processing capability 412. This processor may be, for example, a microprocessor, a digital signal processor (DSP), a field programmable gate array (FPGA), some combination of the these or the like without departing from the scope of the present invention. This system still performs the tasks of processing raw data, displaying data to a user monitor, storing and retrieving data, and optimizing various parameters for dispersion compensation or other affects, but the tasks are split between the processor internal to the OCT imaging system 411 and the computer 410. The tasks can be split in any fashion and may change over time. One possible configuration may be, for example, having the internal processor 412 perform the processing of the raw data and the optimization of the parameters while the computer 410 displays the data to the user monitor and stores and retrieves data.

Figure 5:
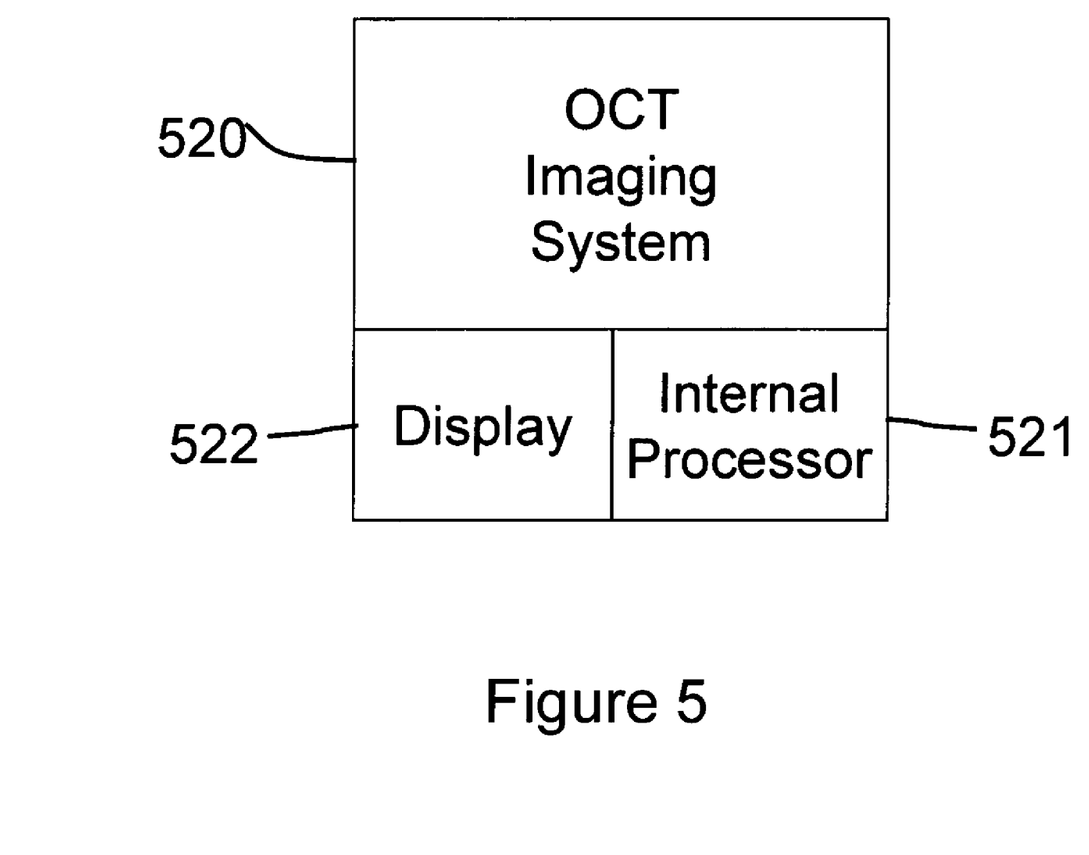
FIG. 5 is a schematic diagram illustrating systems according to some embodiments of the present invention.

Some embodiments of the present invention will now be discussed with respect to FIG. 5. As illustrated therein, the internal processor 521 and the display 522 are provided in the OCT imaging system 520. As discussed above, the processor may be a microprocessor, a DSP, an FPGA, some combination of the these or other processor without departing from the scope of the present invention. According to embodiments of the present invention illustrated in FIG. 5, all tasks may now be performed within the OCT imaging system including processing raw data to create OCT image datasets, for example, A-scans, B-scans and/or volume images, displaying data to a user monitor (or the like), storing and retrieving data, and optimizing various parameters for dispersion compensation or other affects.

Figure 6:
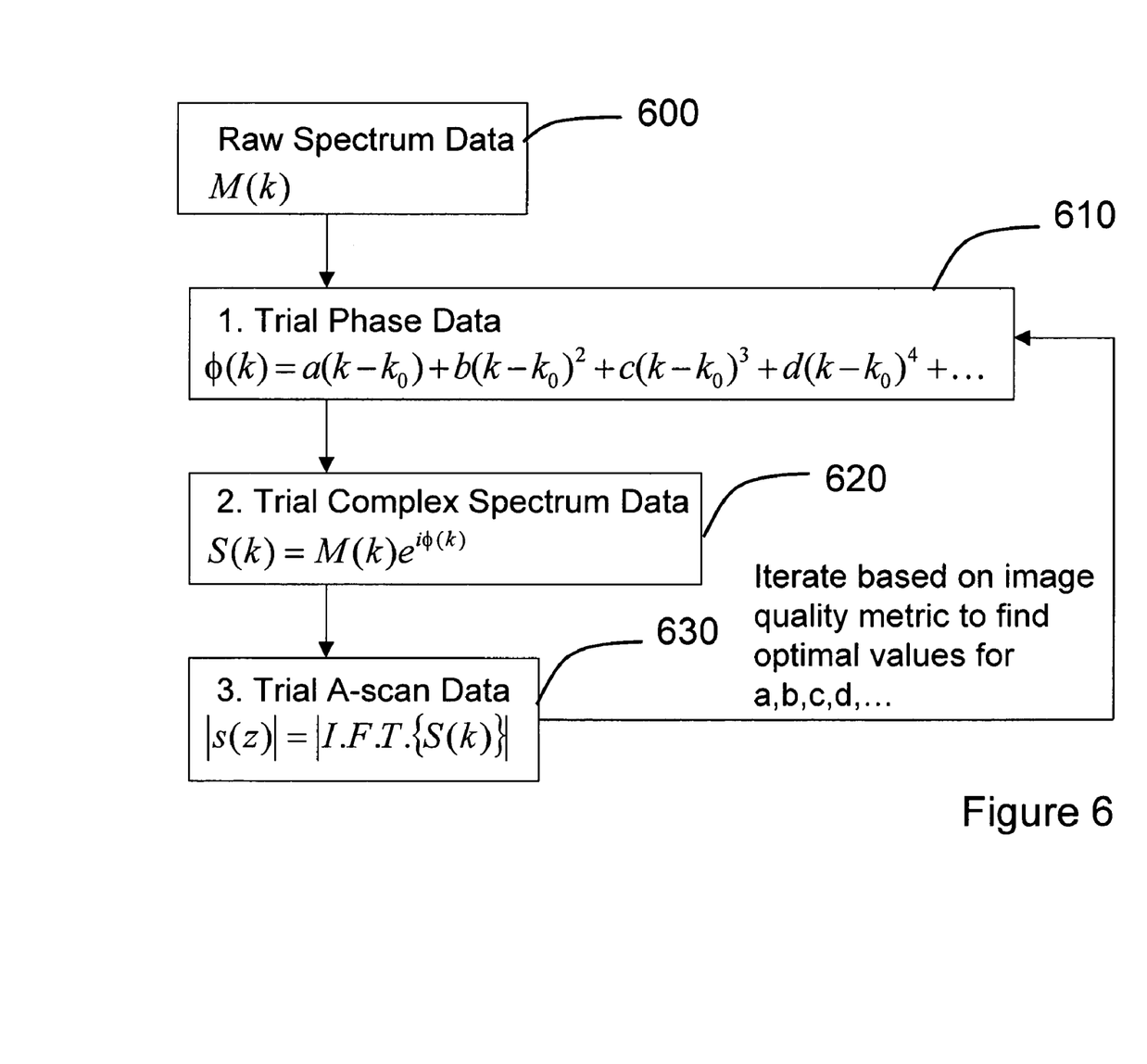
FIG. 6 is a flowchart illustrating operations of OCT imaging methods, systems and computer program products according to some embodiments of the present invention.

Referring now to FIG. 6, a flowchart illustrating algorithms for numerical compensation of dispersion mismatch between the sample and reference arms in Fourier domain optical coherence tomography (FDOCT) systems according to some embodiments of the present invention will be discussed. The FDOCT systems may include spectrometer-based spectral domain optical coherence tomography (SDOCT) and swept-source optical coherence tomography (SSOCT) variants without departing from the scope of the present invention. The algorithm discussed herein according to some embodiments of the present invention may provide advantages over conventional methods, for example, the methods discussed in Chen and Wojtkowski, et. al, the disclosures of which have been previously incorporated herein by reference. For example, use of the algorithm according to some embodiments of the present invention may provide results fast enough for real-time computation and accurate enough results to correct dispersion for all depths in the sample being imaged.

General methods, systems and computer program products for automated numerical dispersion compensation in FDOCT have been discussed above with respect to FIG. 1 through 5. As discussed with respect thereto, automated numerical dispersion compensation in FDOCT may be based upon the optimization of one or more parameters inherent to digital signal processing of FDOCT datasets, which may be based upon optimization of a predetermined image quality metric.

The algorithm illustrated by the flowchart of FIG. 6 illustrates specific embodiments the general methods, systems and computer program products discussed above with respect to FIGS. 1 through 5. In particular, operations begin at block 600 by acquiring raw spectral interferogram data, denoted M(k), for a given lateral position on a sample and a given reference reflection. The variable k represents wavenumber, which is related to optical wavelength according to the relation $k=2\pi/\lambda$, where $\lambda$ is wavelength. The data M(k) represents samples of a continuous real function stored in a computer. In some embodiments of the present invention, the number of samples is a power of 2, such as 1024 or 4096. Furthermore, the spectral interferogram samples may be evenly distributed in k.

As discussed above, some embodiments of the present invention may be used in both SDOCT and SSOCT systems. In SDOCT systems according to some embodiments of the present invention, the data M(k) may be acquired from a spectrometer illuminating a CCD line camera, in which case numerical interpolation may be required to re-sample the original spectral data (which may be evenly sampled in $\lambda$ in the case of grating-based spectrometers) to be evenly sampled in k. In SSOCT systems according to some embodiments of the present invention, the data M(k) may be directly sampled from the output of a single-channel optical receiver.

Operations according to some embodiments of the present invention continue at block 610 by postulating a trial phase corresponding to each wavenumber sample of M(k) according to the following equation:

$$\phi(k)=a(k-k_0)+b(k-k_0)^2+c(k-k_0)^3+d(k-k_0)^4+\ldots \quad \text{Equation (1)}$$

In these embodiments of the present invention, $k_0$ is the central wavenumber of the light source used in the FDOCT system, and the variables a, b, c, d . . . are the parameters to be optimized to improve image quality. The variables a, b, c, d represent first, second, third, and fourth-order corrections to be made to the phase of the spectral interferogram data. As used in the equation set out above, the ellipsis ( . . . ) indicates that more or less orders may be needed in particular situations to achieve a desired image quality result according to some embodiments of the present invention. Typically, at least third-order correction is required for suitable image quality, and rarely are more than ten orders of correction required.

Operations continue at block 620 by assembling the raw spectral data and the trial spectral phase data into the trial complex spectrum data according to the following equation:

$$S(k)=M(k)e^{i\phi(k)}. \quad \text{Equation (2)}$$

In these embodiments, e is the base of natural logarithms and i is the square root of −1. Operations according to some embodiments of the present invention continue at block 630 by computing trial A-scan data by performing an inverse Fourier transform on the trial complex spectrum data and determining the magnitude of the result, according to the following equation:

$$|s(z)|=|I.F.T.\{S(k)\}|. \quad \text{Equation (3)}$$

The result |s(z)| is the real-valued trial A-scan representing the depth-resolved reflectivity of the sample at a given lateral location, blurred by dispersion mismatch between the interferometer arms but corrected by the trial phase postulated in the first step. As illustrated in FIG. 6, operations of blocks 710 through 730 may be repeated to optimize the values for the variables a, b, c, d . . . based on optimization of an image quality metric applied to the trial A-scan data |s(z)|.

It will be understood that a number of parameter optimization techniques may be used to search for the optimal parameters without departing from the scope of the present invention. For example, the value of the first-order parameter a may be optimized by maximizing the image quality metric to some desired accuracy. Then, the value of the second-order parameter b may be optimized in a similar manner, and so on. As discussed above, useful image quality metrics may include the maximum peak value observed in the trial A-scan data |s(z)|, the number of peaks above a specified threshold data, or the narrowness of an individual reflectance peak in |s(z)| arising from a well-defined reflection in a trial sample.

The optimization procedure just described may be applied to individual A-scans, or may alternatively be applied to an entire multidimensional image or volume dataset consisting of many individual A-scans. In these embodiments of the present invention, the same trial phase parameters a, b, c, d . . . are applied for each A-scan in the multidimensional dataset during the optimization procedure, and the image quality metric then corresponds to two (or higher) dimensional metrics, such as the highest peak in a two-dimensional image, the number of peaks above a specified threshold in a two-dimensional image, or the narrowness of an individual reflectance peak in two dimensions.

Once found through the optimization procedure, the optimized parameters a, b, c, d . . . may then be used for fast, real-time processing of each subsequent A-scan acquired for a given imaging geometry according to some embodiments of the present invention. As discussed above, blocks 610 through 630 of FIG. 6 illustrate the steps of the fast dispersion correction algorithm according to some embodiments of the present invention. The optimized parameters a, b, c, d . . . may be used in place of trial parameters. These parameters will be applicable for numerical dispersion compensation until the amount of dispersion in either the sample or reference arm changes appreciably.

As discussed above, some embodiments of the present invention may provide advantages over conventional methods. For example, unlike conventional methods, the algorithm according to some embodiments of the present invention may correct dispersion for all depths in the sample simultaneously, so long as the spectral data is calibrated accurately, and may operate in real time.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for generating parameters for software dispersion compensation in optical coherence tomography (OCT) systems, comprising:
acquiring raw real-valued spectral interferogram data for a given lateral position on a sample and a given reference reflection;
postulating a trial spectral phase corresponding to each wavenumber sample of the acquired real-valued spectral interferogram data without first applying a Hilbert transform or a Fourier transform to the real-valued spectral interferogram data to derive the trial spectral phase;
assembling the acquired raw spectral data and the postulated trial spectral phase data into trial complex spectrum data; and
computing trial A-scan data by performing an inverse Fourier transform on the trial complex spectrum data and determining the magnitude of a result.

2. The method of claim 1:
wherein the raw real-valued spectral interferogram data is denoted M(k); and
wherein postulating comprises postulating a trial phase corresponding to each wavenumber sample of M(k) according to the following equation:

$$\phi(k)=a(k-k_0)+b(k-k_0)^2+c(k-k_0)^3+d(k-k_0)^4,$$

wherein $k_0$ is the central wavenumber of a light source of the OCT system, wherein k is a sample wavenumber, and wherein a, b, c and d are parameters to be optimized and represent respective first, second, third, and fourth-order corrections to be made to a phase of the acquired raw spectral interferogram data.

3. The method of claim 2, wherein assembling comprises assembling the acquired raw real-valued spectral interferogram data and the trial spectral phase data into the trial complex spectrum data according to the following equation:

$$S(k)=M(k)e^{i\phi(k)},$$

wherein e is the base of natural logarithms and i is the square root of −1.

4. The method of claim 3, wherein computing comprises computing trial A-scan data by performing an inverse Fourier transform (I.F.T.) on the trial complex spectrum data and determining the magnitude of the result according to the following equation:

$$|s(z)|=|I.F.T.\{S(k)\}|,$$

wherein the result $|s(z)|$ is the real-valued trial A-scan representing the depth-resolved reflectivity of the sample at a given lateral location, blurred by dispersion mismatch between interferometer arms but corrected by the postulated trial spectral phase.

5. The method of claim 4, further comprising repeating the postulating, assembling and computing steps to optimize the values of a, b, c and d based on optimization of an image quality metric applied to the trial A-scan data $|s(z)|$.

6. The method of claim 5, wherein the image quality metric is applied to $|s(z)|$ for a range of values of depth z for which the result is desired to be independent of depth z and wherein the result $|s(z)|$ is the real-valued trial A-scan representing the depth-resolved reflectivity of the sample at a given lateral location.

7. An optical coherence tomography (OCT) system, comprising:
an imaging system with automatic parameter optimization, the imaging system being configured to:
acquire raw real-valued spectral interferogram data for a given lateral position on a sample and a given reference reflection;
postulate a trial spectral phase corresponding to each wavenumber sample of the acquired real-valued spectral interferogram data, wherein the imaging system is configured to postulate the trial spectral phase without first applying a Hilbert transform or a Fourier transform to the real-valued spectral interferogram data to derive the trial spectral phase;
assemble the acquired raw spectral data and the postulated trial spectral phase data into trial complex spectrum data; and
compute trial A-scan data by performing an inverse Fourier transform on the trial complex spectrum data and determining the magnitude of a result.

8. The system of claim 7, wherein the raw real-valued spectral interferogram data is denoted M(k), the imaging system being further configured to postulate a trial phase corresponding to each wavenumber sample of M(k) according to the following equation:

$$\phi(k)=a(k-k_0)+b(k-k_0)^2+c(k-k_0)^3+d(k-k_0)^4,$$

wherein $k_0$ the central wavenumber of a light source of the OCT system, wherein k is a sample wavenumber, and wherein a, b, c and d are parameters to be optimized and represent respective first, second, third, and fourth-order corrections to be made to a phase of the acquired raw spectral interferogram data.

9. The system of claim 8, wherein the imaging system is further configured to assemble the acquired raw real-valued spectral interferogram data and the trial spectral phase data into the trial complex spectrum data according to the following equation:

$$S(k)=M(k)e^{i\phi(k)},$$

wherein e is the base of natural logarithms and i is the square root of −1.

10. The system of claim 9, wherein the imaging system is further configured to compute trial A-scan data by performing an inverse Fourier transform (I.F.T.) on the trial complex spectrum data and determining the magnitude of the result according to the following equation:

$$|s(z)|=|I.F.T.\{S(k)\}|,$$

wherein the result $|s(z)|$ is the real-valued trial A-scan representing the depth-resolved reflectivity of the sample at a given lateral location, blurred by dispersion mismatch between interferometer arms but corrected by the postulated trial spectral phase.

11. The system of claim 10, wherein the imaging system is configured to repeatedly postulate, assemble and compute steps to optimize the values of a, b, c and d based on optimization of an image quality metric applied to the trial A-scan data $|s(z)|$.

12. The system of claim 11, wherein the image quality metric is applied to $|s(z)|$ for a range of values of depth z for which the result is desired to be independent of depth z and wherein the result $|s(z)|$ is the real-valued trial A-scan representing the depth-resolved reflectivity of the sample at a given lateral location.

13. A computer program product for generating parameters for software dispersion compensation in optical coherence tomography (OCT) systems, the computer program product comprising:

computer readable storage medium having computer readable program code embodied in the medium, the computer readable program code comprising:

computer readable program code configured to acquire raw real-valued spectral interferogram data for a given lateral position on a sample and a given reference reflection;

computer readable program code configured to postulate a trial spectral phase corresponding to each wavenumber sample of the acquired real-valued spectral interferogram data, wherein the computer readable program code configured to postulate the trial spectral phase is configured to postulate without first applying a Hubert transform or a Fourier transform to the real-valued spectral interferogram data to derive the trial spectral phase;

computer readable program code configured to assemble the acquired raw spectral data and the postulated trial spectral phase data into trial complex spectrum data; and computer readable program code configured to compute trial A-scan data by performing an inverse Fourier transform on the trial complex spectrum data and determining the magnitude of a result.

14. The computer program product of claim 13, wherein the raw real-valued spectral interferogram data is denoted M(k), the computer program product further comprising computer readable program code configured to postulate a trial phase corresponding to each wavenumber sample of M(k) according to the following equation:

$$\phi(k)=a(k-k_0)+b(k-k_0)^2+c(k-k_0)^3+d(k-k_0)^4,$$

wherein $k_0$ the central wavenumber of a light source of the OCT system, wherein k is a sample wavenumber, and wherein a, b, c and d are parameters to be optimized and represent respective first, second, third, and fourth-order corrections to be made to a phase of the acquired raw spectral interferogram data.

15. The computer program product of claim 14, further comprising computer readable program code configured to assemble the acquired raw real-valued spectral interferogram data and the trial spectral phase data into the trial complex spectrum data according to the following equation:

$$S(k)=M(k)e^{i\phi(k)},$$

wherein e is the base of natural logarithms and i is the square root of −1.

16. The computer program product of claim 15, further comprising computer readable program code configured to compute trial A-scan data by performing an inverse Fourier transform (I.F.T.) on the trial complex spectrum data and determining the magnitude of the result according to the following equation:

$$|s(z)|=|I.F.T.\{S(k)\}|,$$

wherein the result $|s(z)|$ is the real-valued trial A-scan representing the depth-resolved reflectivity of the sample at a given lateral location, blurred by dispersion mismatch between interferometer arms but corrected by the postulated trial spectral phase.

17. The computer program product of claim 16, further comprising computer readable program code configured to repeat the postulating, assembling and computing steps to optimize the values of a, b, c and d based on optimization of an image quality metric applied to the trial A-scan data $|s(z)|$.

18. The computer program product of claim 17, wherein the image quality metric is applied to $|s(z)|$ for a range of values of depth z for which the result is desired to be independent of depth z and wherein the result $|s(z)|$ is the real-valued trial A-scan representing the depth-resolved reflectivity of the sample at a given lateral location.

* * * * *

UNITED STATES PATENT AND TRADEMARK OFFICE
CERTIFICATE OF CORRECTION

PATENT NO. : 7,719,692 B2  Page 1 of 1
APPLICATION NO. : 11/796399
DATED : May 18, 2010
INVENTOR(S) : Izatt et al.

It is certified that error appears in the above-identified patent and that said Letters Patent is hereby corrected as shown below:

In the Claims:
Column 12, Claim 8, Line 53: Please correct "$k_o$ the" to read -- $k_o$ is the --

Column 13, Claim 13, Line 40: Please correct "Hubert" is read -- Hilbert --

Column 14, Claim 14, Line 9: Please correct "$k_o$ the" to read -- $k_o$ is the --

Signed and Sealed this

Twenty-sixth Day of October, 2010

David J. Kappos
*Director of the United States Patent and Trademark Office*